United States Patent [19]

Rockland et al.

[11] 4,010,758
[45] Mar. 8, 1977

[54] BIPOLAR BODY TISSUE ELECTRODE

[75] Inventors: Ronald H. Rockland, Wayzata; David H. Gobeli, St. Paul, both of Minn.

[73] Assignee: Medtronic, Inc., Minneapolis, Minn.

[22] Filed: Sept. 3, 1975

[21] Appl. No.: 610,063

[52] U.S. Cl. .......................... 128/418; 128/419 P
[51] Int. Cl.² ......................................... A61N 1/04
[58] Field of Search .............. 128/418, 419 P, 404

[56] References Cited

UNITED STATES PATENTS

| | | | |
|---|---|---|---|
| 3,472,234 | 10/1969 | Tachick | 128/418 |
| 3,543,761 | 12/1970 | Bradley | 128/418 X |
| 3,737,579 | 6/1973 | Bolduc | 128/418 |
| 3,750,650 | 8/1973 | Ruttgers | 128/418 X |
| 3,827,428 | 8/1974 | Hon et al. | 128/418 X |
| 3,835,864 | 9/1974 | Rasor et al. | 128/418 X |
| 3,880,169 | 4/1975 | Starr et al. | 128/418 |

FOREIGN PATENTS OR APPLICATIONS

| | | | |
|---|---|---|---|
| 1,277,107 | 6/1972 | United Kingdom | 128/418 |

Primary Examiner—Robert W. Michell
Assistant Examiner—Lee S. Cohen
Attorney, Agent, or Firm—Cameron, Kerkam, Sutton, Stowell & Stowell

[57] ABSTRACT

A bipolar electrode of the type adapted to be electrically and physically coupled to a body tissue is disclosed as comprising a helix-configured electrode to be screwed into the body tissue and an annular-shaped electrode disposed about the helical electrode for surface contact with the tissue, and first and second flexible electrodes coupled respectively to the aforementioned electrodes. Each of the flexible electrodes has a proximal end adapted for connection to a power supply and a distal end portion for connection to the one of the aforementioned electrodes. The helix-configured electrode is partially covered with an inert insulating material with the tip of the helical electrode being exposed. The annular-shaped electrode is disposed about the helical electrode whereby an intense field is formed between the annular-shaped electrode and the exposed tip of the helical electrode, thus insuring efficient stimulation of the tissue and minimum current drainage of the power supply, e.g. a battery.

14 Claims, 8 Drawing Figures

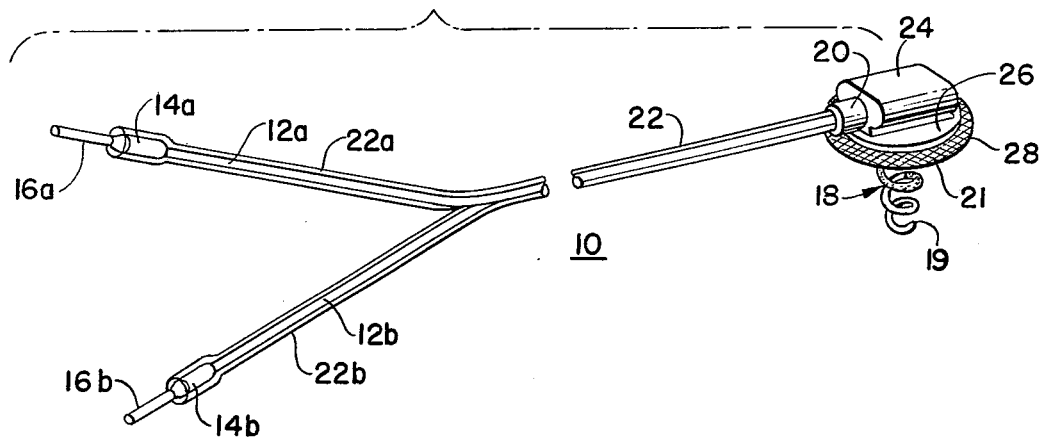
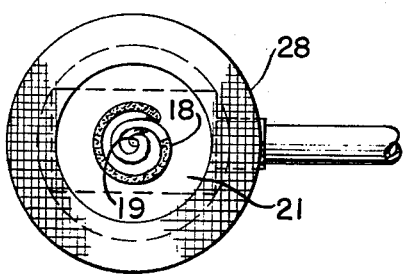
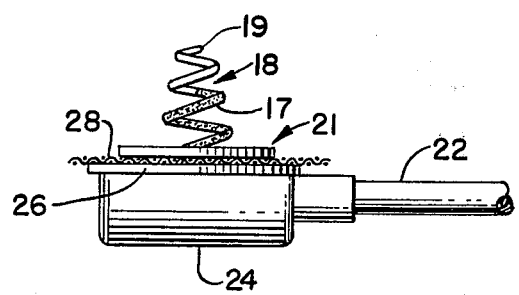
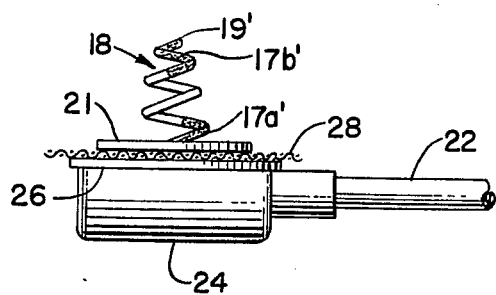

BIPOLAR BODY TISSUE ELECTRODE

CROSS-REFERENCE TO RELATED APPLICATIONS

Reference is made to the following, co-pending application assigned to the assignee of this invention:

Application Ser. No. 487,241, entitled "Arrhythmia Prevention Apparatus", filed July 10, 1974 in the name of Herman P. Funke, M. D.

BACKGROUND OF THE INVENTION

1. Field of the Invention

This invention relates to the field of medical electronics and particularly to a bipolar electrode adapted for being electrically and structurally connected to body tissue such as the heart.

2. State of the Prior Art

Electrical stimulation of body tissue and organs as a method of treating various pathological conditions is becoming quite common-place. Such stimulation generally entails making some type of electrical contact with the body tissue or organ. In particular, with respect to the heart, electrical leads have been thoracotomy in which an electrode formed on the end of the lead are physically implanted into the myocardial tissues.

Various electrode structures and various techniques for implanting those electrode structures into such body tissue as the heart or myocardium, have been developed. Typically, electrodes attached to the heart are stimulated by a cardiac pacemaker which may be implanted within the patient's body. Previously, a thoractomy was commonly required to attach the cardiac pacemaker leads to the heart, and the electrical leads were sutured into electrical contact with the heart. This technique has numerous disadvantages. Firstly, a thoracotomy, which requires a large incision in the chest or thorax, is drastic surgery and has a relatively high mortality rate. Secondly, suturing the electrical leads into electrical contact with the heart causes severe trauma to the heart, which it is desirable to minimize.

An intravenous connection has also been used to attach electrical leads of a cardiac pacemaker to the heart. In this technique, the electrical lead is passed through a vein into the heart where it is held by fibrilla located in close proximity to the heart valve through which the lead is passed. There are, however, many disadvantages to this technique also, including: the possibility of damage to the vein during insertion, such as vein perforation; the failure to attach securely the electrical lead to the heart; the possibility of perforating the heart wall with the electrical lead during insertion or after attachment has been completed; and the possibility of improper lead placement in the heart.

Other techniques have included the percutaneous insertion through the chest wall or an open wound by means of a hollow needle with the subsequent placement of the electrode into the myocardial tissue. Still another technique involved the deformation or flattening of one convolution of a rigid helix serving as the electrode so that a keyed stylet could engage the deformed convolution to permit the electrode to be screwed into the myocardial tissue. However, this technique requires that the stylet be in physical contact with the helix during insertion into the myocardium and in addition has the undesirable effect of imparting torque to the proximal end of the coiled conductor.

In U.K. Pat. No. 1,277,107, there is described an electrode taking the form of a helically-shaped member and a tool for rotating the helically-shaped electrode whereby it is screwed into body tissue, e.g. the myocardium. In one disclosed embodiment, two such helically-shaped electrodes are inserted into the heart, whereby stimulating pulses are applied thereto from a cardiac pacemaker implanted within the patient's body. Further, there is disclosed an electrode assembly whereby two helically-shaped electrodes are intertwined between each other. Each of the helically-shaped electrodes has tipped portions whereat the electrical insulating material is removed, with the electrically-bared portions of the electrodes displaced from each other whereby a field is established therebetween.

In U.S. Pat. No. 3,737,579, assigned to the assignee of this invention, there is disclosed a unipolar body tissue electrode comprising an uninsulated, conductive, rigid helix adapted for attachment to body tissue and a flexible insulated conductor having a proximal end adapted for connection to a power supply and a distal end for connection to the helical electrode. In electrodes particularly adapted for use with cardiac pacemakers, there are particular problems heretofore unresolved.

Further, it is desired to use a plurality of electrodes to tend to prevent arrhythmias such as described in the above-identified Funke patent application. In particular, it would be undesirable to use two distinct electrodes at each point of stimulation or detection in that the number of electrodes as well as the surgical steps required to implant a plurality of electrodes are increased. As the number of electrodes is increased, the size of the surgical opening into the patient's body, the number of wounds into the heart and the resultant trauma of the entire surgical procedure are increased.

It is contemplated that the bipolar electrode structure including the double-helix electrodes of U.K. Pat. No. 1,277,107, could be utilized whereby the number of electrodes required for multi-electrode stimulation would be reduced. However, there are several significant problems resulting from the use of such a structure. First, the electrical insulation separating the intertwined electrodes may tend to deteriorate with age, especially within the environment of a living organism. The second of the intertwined electrodes having an unshielded portion displaced from the tip of the forwardmost helical electrode has a limited exposed area that is disposed at the epicardium of the heart. It is expected that after such an electrode structure has been implanted within a patient for several years that the surrounding portion of the myocardium would become ischemic or infarcted, thus blocking or reducing the electrical field established between the exposed portions of such an electrode structure. Eventually, it is contemplated that the resultant electric field would become so weak to be incapable of stimulating the heart, especially as the energy level of the power source, e.g. a battery, attenuates with extended life.

A further problem associated with cardiac pacemakers relates to the dissipation of the pacemaker batteries with extended life. After a period of time, e.g. 2 to 4 years, the implanted pacemaker must be removed and its batteries replaced. Therefore, it is desirable to reduce the current drain by appropriate design of the pacemaker's electrodes, whereby the battery life is extended, while maintaining the strength of the resultant electric field through the myocardium at a sufficiently high level to stimulate the heart.

SUMMARY OF THE INVENTION

It is therefore an object of the present invention to provide a bipolar electrode device suitable for multielectrode stimulation of body tissue, typically the myocardium, whereby blood circulation efficiency is improved.

It is a further object of this invention to provide a bipolar electrode adapted to be readily and easily inserted into body tissue for providing a relatively intense electric field therebetween, while placing a relatively low current drain upon its associated power source.

It is a still further object of this invention to provide a bipolar electrode structure adapted to reduce the effect of localized ischemic or infarcted tissue area upon the field produced by such an electrode structure.

In accordance with these and other objects, there is provided in accordance with the teachings of the present invention a bipolar electrode structure comprising a first, helix-configured electrode adapted to be implanted within the body tissue, e.g. the heart, by rotation or screwing and a second, annularly-shaped electrode disposed substantially concentric about the first electrode upon the surface of the tissue, e.g. the epicardium. The first helical electrode is covered with an inert insulating material, except for an exposed tip thereof. Further, there is provided two flexible, insulated conductors, each having a distal end adapted to be connected to one of the first and second electrodes, and a proximal end adapted to be connected to a suitable power source such as a cardiac pacemaker. The described electrode configuration is particularly adapted to provide a very intense electric field between the second, annularly-shaped electrode and the exposed tip of the first, helical electrode. Further, the relatively large area presented by the second, annularly-shaped electrode substantially prevents a field reduction due to the formation of ischemic or infarcted areas upon the epicardium.

BRIEF DESCRIPTION OF THE DRAWINGS

These and other objects and advantages of the present invention will become more apparent by referring to the following detailed description and accompanying drawings, in which:

FIG. 1 is a perspective view of the bipolar electrode structure of this invention;

FIGS. 2A, 2B and 2C are, respectively, a bottom plan view of the electrode structure shown in FIG. 1, and side views of the electrode structure as shown in FIG. 1 and of a further embodiment of this invention;

DESCRIPTION OF THE PREFERRED EMBODIMENT

Figure 3:
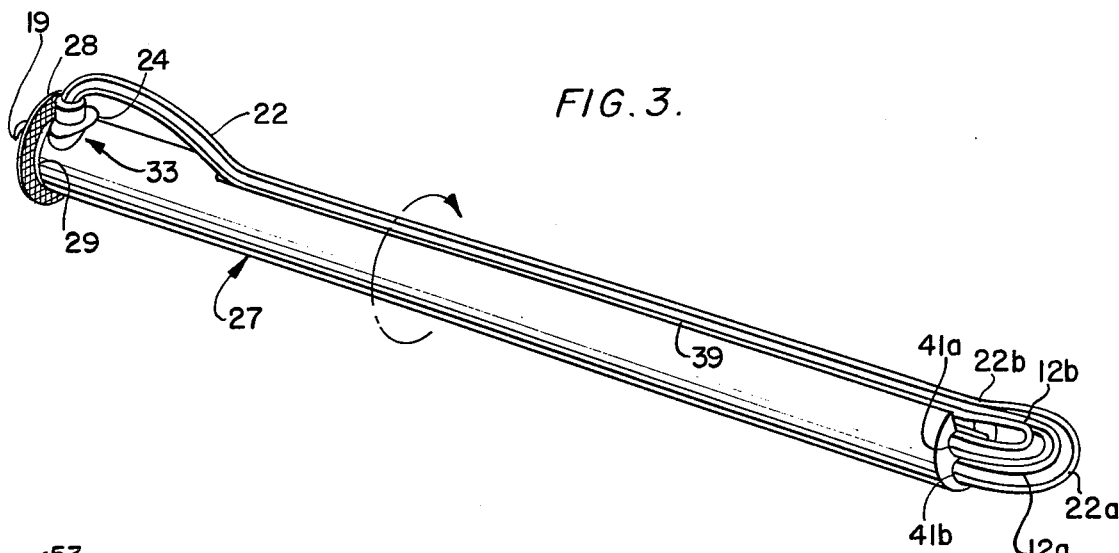
FIG. 3 is a perspective view of a primary work device or tool for rotatably planting or screwing the electrode structure of FIGS. 1 and 2 into body tissue.

In FIG. 1, there is shown an implantable bipolar electrode structure 10 in accordance with the teachings of this invention, which includes first and second flexible, electrical conductors 12a and 12b. Each conductor 12 may, for example, be made of wrapped platinum wire or other suitable conducting material adaptable to the internal environment of a human or animal body. Wrapped platinum wire is generally comprised of a plurality of platinum ribbons, each helically wound around a separate electrically non-conductive core and then all the platinum ribbons are helically wound around a central electrically non-conductive core. A specific description of this type of conductor may be found in U.S. Pat. No. 3,572,344, issued Mar. 23, 1971, and entitled "Electrode Apparatus With Novel Lead Construction".

Affixed to the proximal end of conductor 12a is an electrical connector 14a having a tip or extension 16a which may be connected to a suitable implantable or external power supply. Affixed to and serving as the distal end portion of conductor 12a is a rigid helical electrode 18 having several convolutions. Helical electrode 18 is a rigid coil which may, for example, be made of platinum irridium, and terminates in a sharply pointed end 19. Electrode 18 serves as the distal end portion of conductor 12a which may be screwed into body tissue, as will be explained later. Electrode 18 and conductor 12a are electrically joined together by conductive epoxy (not shown) substantially orthogonally with respect to one another and this electrical junction is contained in a rubber boot 20.

Conductor 12a, connector 14a and boot 20 are covered with a relatively transparent, flexible insulating covering being relatively inert with respect to the body, which, for example, may be a silicone rubber casing 22. The portion of casing 22 surrounding boot 20 forms a raised portion or silastic housing 24. The distal portion of casing 22 is terminated and shaped as a circular disc 26 through which helical electrode 18 projects. Helical electrode 18 projects through disc 26 at substantially a right angle to its conductor 12a. Affixed to the under surface of disc 26 is a circular sheet of netting 28, which may, for example, be made of Dacron, which is a trademark of E. I. DuPont De Nemours and Company for a type of polyester fiber. Netting 28 enhances fibrotic growth, further insuring a secure connection of the electrode to the tissue.

Further, the bipolar electrode structure 10 includes a second, flexible electrical conductor 12b similar to that conductor 12a described above in detail. In particular, the conductor 12b extends through casing 22 in an insulated fashion with respect to conductor 12a. As shown in FIG. 1, the casing 22 includes a first bifurcated portion 22a, through which conductor 12a extends and a second bifurcated portion 22b, through which conductor 12b extends. The conductor 12b includes an electrical connector 14b having a tip or extension 16b which may be connected to a suitable implantable or external power supply. The distal end of conductor 12b is electrically connected to an annularly-shaped, plate-like electrode 21. In those situations where the bipolar electrode structure 10 is coupled to the patient's heart, the first, helical electrode 18 is adapted to be rotatively implanted or screwed into the endocardium of the heart, whereas the exposed, bottom surface of the second, annularly-shaped electrode 21 is adapted to lay upon the external surface or epicardium of the heart.

Many advantages reside in the configuration of the bipolar electrode structure 10 as described above. First, the first or endocardial electrode 18 is of a helical configuration, whereby it is particularly adapted to be rotatively inserted or screwed into body tissue. As will be described in detail later, such a procedure is readily accomplished with a minimal incision into the body tissue, thus reducing the trauma imposed upon the patient. In addition, the insertion of such a helical electrode 18 does not require a large exposed surface of tissue, thus minimizing the size of the surgical opening required to permit access for the surgeon to the tissue.

Further, the combination of the helical electrode 18 and the annular plate 21 insures an intense field therebetween that is primarily directed through the body tissue, e.g. the myocardium, thus causing efficient stimulation of the heart. As explained above, the first helical-shaped electrode 18 is inserted into the endocardium, whereas the bottom surface of the second, annularly-shaped electrode 21 is disposed in intimate contact with the epicardium, whereby the field produced therebetween is concentrated within the myocardium. As more clearly shown in FIG. 2B, the helical electrode 18 is covered with a suitable inert, insulating material 17 as described above. The insulating covering 17 covers most of the helical electrode 18, leaving exposed a portion thereof associated with the pointed tip 19. The insulating covering 17 tends to limit the field emanating from the helical electrode 18 to the exposed portion about the tip 19, thus increasing the intensity of the field. In particular, the field tends to form between the bottom-most surface of the annularly-shaped electrode 21 and the exposed portion about the tip 19 of the helical electrode 18, whereby an intense field is formed radiating from the tip 19 toward the relatively large area presented by the annularly-shaped electrode 21. As a result, the energization in terms of voltage or current from the associated power source is minimized. In those applications wherein the bipolar electrode assembly 10, as described above, is energized by a cardiac pacemaker, a minimum current drain is placed upon the battery source of the cardiac pacemaker whereby the battery life is significantly extended.

By contrast to the use of two distinct electrodes as suggested by the prior art, the exposed areas of electrodes 18 and 21 are disposed relatively close to each other whereby the intense field is generated through the myocardium. The electrode arrangement as taught herein is advantageous with respect to the use of two distinct electrodes wherein an intense field is not directed through the body tissue, e.g. the myocardium.

The size of the exposed portion of helical electrode 18 is made sufficiently small so as to concentrate the field emanating from the tip 19 establishing a relatively intense electric field. On the other hand, enough area of electrode 18 must be exposed in order that a sufficient mass of body tissue, e.g. the myocardium, may be stimulated. In one illustrative embodiment, a length of the helical electrode in the range of about 0.03 in. to 0.07 in. was left exposed.

In addition, the size of the annularly-shaped electrode 21 may be increased without significantly affecting the intensity of the field which is concentrated at the exposed tip 19 of the helical electrode 18. As a result, the size of the annularly-shaped electrode 21 may be made relatively large to minimize the effect of infarcted or ischemic tissue upon the stimulating field. It is contemplated that such tissue may develop about the area of implantation after the electrodes have been attached, thus tending to provide a high impedance to the field. However, due to the relatively large surface area from which the field emanates, it is not contemplated that the entire area of the annularly-shaped electrode 21 would be blocked. In any event, it is contemplated that the field emanating from the annular electrode 21 would circumvent the infarcted or ischemic tissue. As a result, the resultant field would be sufficient to stimulate the patient's heart, regardless of the formation of such tissue and without unduly draining the bipolar electrode's power source.

It is contemplated that the size of the electrodes may vary, dependent upon their application. For example, as explained above, the size of the annularly-shaped electrode 21 may be increased in those situations where it is contemplated for use in an environment where ischemic or infarcted tissue may develop; for example, the inner and outer diameters of the annularly-shaped electrode 21 may be dimensioned in the range of 0.15 in. to 0.22 in., and 0.36 in. to 0.43 in., respectively. Further, the length of the helical-shaped electrode 18 may vary, dependent upon the tissue into which it is to be inserted. For example, with use with a cardiac pacemaker, it is contemplated that the electrode 18 may be inserted into various portions of the heart. For example, if the electrode 18 were to be disposed into the right ventricle of the heart, an electrode 18 of an axial length in the order of 0.16 in. to 0.20 in. could be used, whereas if a helical electrode 18 were to be disposed into the left ventricular apex having a thicker wall, a slightly longer electrode 18 may be employed, having an axial length in the order of 0.20 in. to 0.24 in.

A further, alternative embodiment of this invention is illustrated in FIG. 2C, showing a helically-shaped electrode 18' covered with first and second layers 17a' and 17b' of an inert insulating material over the uppermost and lowermost portions thereof, leaving exposed an intermediate portion of the helical electrode 18'. It is contemplated in those applications where the body tissue to be stimulated is relatively thin, that an intermediate portion of the helical electrode 18' would be left exposed, insuring that the electric field established between the helical electrode 18' and the annular electrode 21 is confined to the tissue to be stimulated, e.g. the myocardium, while insuring that a maximum length of the electrode 18' is inserted into the tissue to insure a firm electrode assembly attachment thereto.

The method and apparatus for rotatively inserting or screwing the bipolar electrode structure 10 into body tissue will now be described; reference is made to U.S. Pat. No. 3,875,947, entitled, "Device For Screwing Body Tissue Electrode Into Body Tissue An Article Usable Therewith", by James Jula and Dennis Zeidler, for further details of the apparatus and method. With respect to FIGS. 3 to 6, there is shown a primary device or tool 27 and an auxiliary device 43 for receiving and inserting the electrode assembly 10. In particular, the device 27 is adapted to hold lead 22 at four places; the housing 24, casing 22 and connectors 14a and 14b. Device 27 comprises a substantially cylindrically-shaped body 25 having a longitudinal axis 23 and end surfaces 29 and 31. Device 27 may be made, for example, of a hard plastic material such as Delrin, a trademark of the E. I. DuPont DeNemours and Company for acetal resins. Preferably, device 27 should be made of an autoclavable material. Formed in end surface 29 is a slot 33. Slot 33 includes a frontal opening 35 leading to a cavity 37. The width of cavity 37 is greater than the width of frontal opening 35. The widths of frontal opening 35 and cavity 37 are selected such that housing 24 must be laterally compressed to a slight degree in order to pass through frontal opening 35. Once at least a portion of housing 24 is past the shoulders 38, that portion resumes its original shape. To remove housing 24 from slot 33 requires recompressing such portion in order to gain withdrawal from frontal opening 35. The shape of slot 33 and housing 24 is designed such that the force required to achieve the requisite compressive state is greater than the forces that might be encountered in the implantation procedure, but insufficient to disturb the implanted electrode 18 as the housing 24 and slotted end 29 are being separated. Formed in the outer surface of device 27, lying in a plane substantially parallel to axis 23, and extending from end surface 31 for substantially the entire length of device 27, is a groove 39. Groove 39, which is substantially aligned with slot 33, is adapted to receive and securely engage at least a portion of the length of casing 22. End surface 31 includes a slot 40 which communicates with a first bore 41a. The first bore 41a includes a first section 42a which extends slightly beyond groove 39 and a second section 44 of reduced diameter which is concentric with section 42a. Further, as shown in FIG. 3, there is included a second bore 41b disposed substantially parallel with the first bore 41a within the device 27, and including a section 42b of a corresponding length to that of section 42a. Sections 42a and 42b of bores 41a and 41b are adapted to receive, respectively, at least a portion of the bifurcated portions 22a and 22b, including connectors 14a and 14b, and tips 16a and 16b. Only bore 41a communicates with groove 39 the entire length of groove 39. At the approach to end 29, groove 39 provides a terminal portion 45 which slants downward towards end 29 until it merges with bore 41a. As will be seen hereinafter, this terminal portion of groove 39 is shaped to accommodate the terminal portion of an auxiliary tool 43. The cross-sectional dimension of groove 29 is preferably less than the cross-sectional dimension of section 42a of bore 41a. Groove 39 is wide enough to receive and hold casing 22, yet preferably not so wide that casing 22 is able to drop into section 42a of bore 41a.

Figure 4:
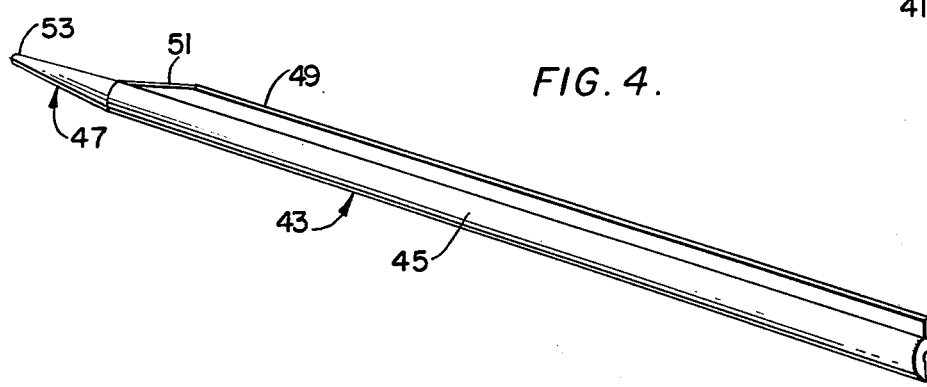
FIG. 4 is a perspective view of the auxiliary device operative in connection with the primary tool of FIG. 3.

In FIG. 4, there is shown the auxiliary tool 43 for use in combination with the primary device 27. Tool 43 includes a substantially cylindrical body portion 45, a terminal portion 47, and a ridge portion 49. Body portion 45 is designed to slide freely in bore 41a of device 27. As body portion 45 advances in bore 41 from end 31 to end 29, ridge portion 49 simultaneously advances in groove 39. Ridge portion 49 should be of such a size and shape that it is freely slidable in groove 39 and will push or wedge the casing 22 out of groove 39 as it slides along. Ridge portion 49 is preferably relatively thin, with flat, parallel side walls. The leading edge 51 of ridge portion 49 preferably slants downwardly to meet body portion 45 at the terminal portion 47. Terminal portion 47 is tapered to a centered point 53. This allows the casing 22 to be pushed forward and upward out of groove 39 rather than just forward. Terminal portion 47 is generally conically-shaped with the cone apex (end 53) being sufficiently blunt so that it will push rather than penetrate housing 24 in slot 33. The terminal portion 47 is preferably of such a size and shape that the length thereof which will extend from the end of section 44 of bore 41a is approximately equal to or slightly longer than the depth of cavity 37.

Auxiliary tool 43 may be constructed of the same material as device 27.

Figure 5:
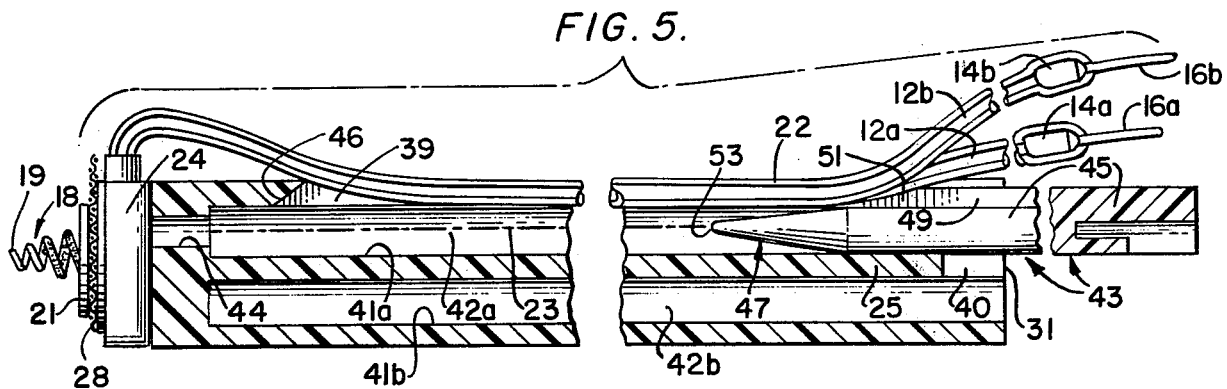
FIG. 5 is a transverse, sectional view of the primary and auxiliary devices as shown in FIGS. 3 and 4.
Figure 6:
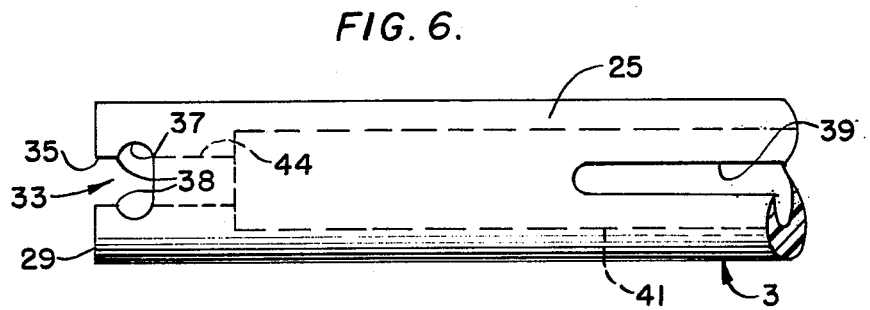
FIG. 6 is an enlarged top view of the working end of the primary device of FIG. 3.

FIG. 5 depicts the primary device 27 of FIG. 3 gripping the casing 22 at the slotted end 33 and partially along groove 39. Tool 43 has been inserted in bore 41a and advanced partially therealong towards slot 33. That segment of casing 22 previously located in the section of groove 39 which has been traversed by ridge portion 49 has been displaced from groove 39 whereas the remainder of casing 22 as well as housing 24 await displacement as tool 43 advances.

In explanation of the manner of using the present invention, the first step is to secure the casing 22 to the device 27 as shown in FIG. 3. The raised portion of the housing 24 is fitted into frontal opening 35 with compression and then at least a portion of housing 24 pushed into cavity 37 to provide a secure hold of housing 24.

A small loop is left in the portion of casing 22 immediately proximal to housing 24 and then casing 22 is worked into groove 39 so as to be securely held in the groove against movement. Then connectors 14a and 14b, and tips 16a and 16b are doubled back for insertion into bores 41a and 41b, respectively, as far as they will go. In this position, the helically-shaped electrode 18 is positioned substantially parallel to longitudinal axis 23 of device 27 and the assembly is now ready for the electrode to be screwed into body tissue.

Pointed end 19 is placed against the tissue or organ and device 27 is rotated as indicated by the curved arrow. The diameter of the wound is confined to the diameter of the wire of which helically-shaped electrode 18 is formed. As device 27 is rotated, helical electrode 18 is firmly screwed into the tissue or organ until netting 28 firmly contacts the outer surface of the organ. Netting 28 helps to provide a more secure and permanent placement of helical electrode 18 in the tissues in that the netting promotes more rapid fibrosis in and around the netting, as well as around the casing 22, thus avoiding the use of suturing techniques and their resultant trauma.

When electrode 18 is firmly screwed into the tissue and netting 28 is firmly seated against the outer surface of the tissue or organ, the connector end of casing 22 is removed from the bores 41a and 41b. Then, the auxiliary tool 43 is utilized as described above to progressively remove the portion of casing 22 lying in groove 39, and then the housing 24 held in slot 33, thereby freeing casing 22 from device 27. With the use of the implantation procedure described, since housing 24 and a substantial portion of casing 22 are firmly secured during the rotation of device 27, no torque is transmitted to casing 22 and consequently to conductors 12a and 12b. In addition, before, during and after the insertion procedure, device 27 in no way contacts the helical convolutions of electrode 18, thus permitting a very positive action in screwing helical electrode 18 into the tissue at substantially a 90° angle.

Thus, there has been disclosed a bipolar electrode assembly particularly adapted to be rotatively inserted into body tissue, e.g. the myocardium, whereby an intense electric field is applied through the tissue while imposing a relatively small current drain upon the associated power source, e.g. the battery for a cardiac pacemaker. As explained above, an electric field is established between an exposed, limited portion of the first helical electrode and the annular-shaped electrode; the established field is relatively intense and is confined to the body tissue due to the particular design of the electrode assembly. Further, the use of the bipolar configuration results in a relatively small incision into the tissue and further, the use of the above-described work devices requires a relatively small surgical opening, whereby patient trauma is significantly reduced. Further, the use of the above-described bipolar electrode assembly reduces the number of electrodes required and facilitates multiple electrode stimulation, whereby the efficiency of the heart is increased and the possibility of serious arrhythmias is reduced or prevented. For a further explanation of multi-electrode heart stimulation, reference is made to the above-identified, co-pending application of Funke et al.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. A heart tissue implantable bipolar electrode assembly for disposition within a living animal comprising:
   a. first and second insulated, flexible conductors, each having a proximal end adapted to be connected to an energizing source and a distal end;
   b. a first conductive, rigid, helically-shaped electrode adapted to be rotatively inserted within the tissue and having a proximal end electrically connected to said distal end of said first conductor;
   c. an inert insulating covering disposed about said first electrode leaving a limited portion thereof exposed;
   d. a second conductive, annularly-shaped electrode disposed about said first electrode and being electrically connected to said distal end of said second conductor, said second electrode having a substantially flat surface adapted for intimate contact with the tissue; and
   e. insulating housing means for mounting said second electrode in a spaced, insulated manner with respect to said first electrode and to dispose said limited portion of said first electrode in a spaced relationship from said flat surface so that said first electrode may be fully inserted within the tissue and said second electrode be in electrical contact with the surface of the tissue, whereby a relatively intense electrical field is established through the tissue between said exposed portion of said first electrode and said second electrode.

2. The electrode assembly as claimed in claim 1, wherein said insulating housing means is disposed about the points of interconnection between said first and second conductors and said first and second electrodes, respectively, and made of a material substantially inert to body fluids.

3. The electrode assembly as claimed in claim 2, wherein said insulating housing means has an exterior surface adapted to be grasped by tool-like means whereby said first, helically-shaped electrode may be rotatively inserted within the tissue while preventing the transmission of torque to said first and second conductors.

4. The electrode assembly as claimed in claim 2, wherein said insulating housing means includes means for supporting only said proximal end of said first electrode so that upon its insertion within the tissue, the electric field established between said first and second electrodes is directed through the tissue.

5. The electrode assembly as claimed in claim 4, wherein there is further included an insulating casing disposed about said first and second flexible conductors, insulating one from the other.

6. The electrode assembly as claimed in claim 1, wherein there is included a mesh-like element supported by said insulated housing means remotely of said second electrode with respect to said first electrode whereby fibrotic growth is enhanced with respect to the tissue, for securing said electrode assembly thereto.

7. The electrode assembly as claimed in claim 1, wherein said first electrode includes a point, said insulating covering leaving said point as said limited exposed portion.

8. The electrode assembly as claimed in claim 1, wherein said first electrode includes a point and said limited exposed portion thereof is disposed intermediate said point and said electrical connection between said first electrode and said first conductor.

9. A heart tissue implantable bipolar electrode assembly comprising:
   a. a first conductive, rigid, helically-shaped electrode adapted to be rotatively inserted within the tissue and having an exposed portion;
   b. a second conductive, annularly-shaped electrode disposed about said first electrode, having a substantially flat surface for intimate electrical contact with the tissue;
   c. insulated means for electrically connecting an energizing source across said first and second electrodes, whereby an electric field is established between said exposed portion of said first electrode and said second electrode;
   d. means for confining the electric field established between said first and second electrodes; and
   e. means for mounting said first and second electrodes in a spaced, insulating manner to dispose said exposed portion of said first electrode in a spaced relationship from said flat surface of said second electrode so that said first electrode may be fully disposed within the tissue and said second electrode be in contact electrically with the surface of the tissue to establish an electrical field through the tissue.

10. The electrode assembly as claimed in claim 9, wherein said mounting means engages a limited end portion of said first electrode, leaving the remaining portion of said first electrode free to be fully inserted within the tissue.

11. The electrode assembly as claimed in claim 10, wherein said mounting means includes means engagable by a tool-like device, for rotatively inserting said first electrode into said tissue and for preventing the transmission of the resulting torque to said connecting means.

12. The electrode assembly as claimed in claim 9, wherein said confining means comprises an insulating covering disposed about said first electrode, leaving a limited portion thereof exposed.

13. The electrode assembly as claimed in claim 12, wherein said first electrode includes a tip, said insulating covering leaving said tip as said limited, exposed portion.

14. The electrode assembly as claimed in claim 12, wherein said first electrode includes a tip and said limited exposed portion is disposed intermediate said tip and said connecting means.

* * * * *